(12) United States Patent
Pollard

(10) Patent No.: US 7,118,211 B1
(45) Date of Patent: Oct. 10, 2006

(54) COMFORT OPTICS VISOR

(76) Inventor: Stephen Leroy Pollard, 27703-14 Ortega Hwy., San Juan Capistrano, CA (US) 92675

( * ) Notice: Subject to any disclaimer, the term of this patent is extended or adjusted under 35 U.S.C. 154(b) by 0 days.

(21) Appl. No.: 09/388,069

(22) Filed: Sep. 1, 1999

(51) Int. Cl.
*G02C 3/00* (2006.01)

(52) U.S. Cl. ...................................... 351/156; 351/158
(58) Field of Classification Search ................ 351/156, 351/158, 41, 157; 381/111
See application file for complete search history.

(56) References Cited

U.S. PATENT DOCUMENTS 5,642,178 A * 6/1997 Leonardi et al. ............ 351/111
5,920,371 A * 7/1999 Chang et al. ................ 351/156

* cited by examiner

*Primary Examiner*—Hung Xuan Dang
(74) *Attorney, Agent, or Firm*—Joseph E. Mueth

(57) ABSTRACT

The comfort optics visor was designed for people who suffer from impaired vision. Both primary and only peripheral vision can be helped, when the comfort optics visor is equipped with 2x to 10x power monoculars, with extra close focus and roof top prisms. The patient has assisted vision without being strapped with tunnel vision. By tipping the head approximately 15 degrees they are aligned. Patient is assisted by the optical assistant, who instructs the patient in the selection of the proper monoculars. He also instructs the patient in alignment and adjustments. The optical technician, while fitting the self-aligning headband and visor, installs the monocular temporary hardware. When the alignment and adjustments are completed, the technician secures the monoculars permanently, and removes the temporary hardware. The patient only has to focus the monoculars to the depth they wish to view.

3 Claims, 9 Drawing Sheets

Front View of Headband

Front View of Visor

Top View of Headband

Side View of Headband

Front View of Alignment Adjuster

Front View of Alignment Clamp

Top View of Beveled Adjuster

Side View of Beveled Adjuster

COMFORT OPTICS VISOR

BACKGROUND OF THE INVENTION

Field of the Invention

Description of the Related Art

The only related art is U.S. Pat. No. 5,920,371. Some of the pieces of art work are similar in that both invention use a visor to hold them on the person's head (this visor is not the subject of either patent as there are many brands of visors available and neither that inventor or I am claiming to have developed the visor. The part of my device that is unique, and therefore patentable, is the alignment device which is very different from the alignment device shown in U.S. Pat. No. 5,920,371. My device is designed to allow the patient to adjust the alignment him or herself, with no help from a caretaker or doctor. The alignment device shown in the prior art could not be adjusted by the patient. My invention features the elongated ports in the visor which work with my unique alignment fixture, a clamp, to allow the patient to adjust the vision simply by applying pressure to the expansion loop. The prior art has a very different alignment fixture and this is the key to the difference in the two inventions.

BRIEF SUMMARY OF THE INVENTION

When pressure is applied to the expansion loop, the headband expands, the pressure may be applied by hand, a surgeon's arm, or by another person (a caretaker for a disabled person, e.g.). When the pressure is released, the headband contracts and the (2) bands on either side of the head align the visor optically the same way every time. No further adjustment need be made for perfect optical alignment.

My application for a patent concerns the expansion loop, which is totally new. Headbands and visors have been made for a long time. Many brands already exist and my invention does not affect those already existing patents. I have developed a unique concept for an expansion loop that provides optical alignment every time pressure on it is removed and replaced.

BRIEF DESCRIPTION OF SEVERAL VIEWS OF THE DRAWING

The following describes the drawings of my invention fully.

Figure 1:
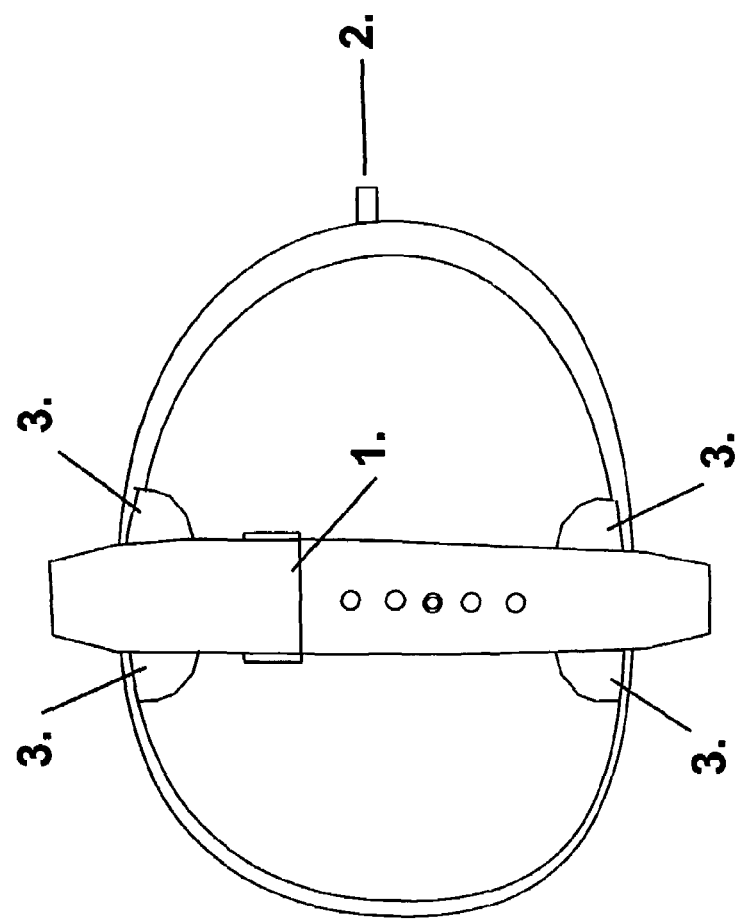
FIG. 1: The top view of the headband shows an expansion loop (right on top of band). The fastener that allows the adjustment and secures the headband to the expansion loop. This part is adjustable so it will fit the patient's requirements.

This is a utility claim, not a design claim, everything herein has been reduced to practice.

DETAILED DESCRIPTION OF THE INVENTION

The comfort optics visor is a novel unique optical device, never offered before, its novel and unique features are as follow 1. The patient is not strapped with tunnel vision. They have their normal vision and get assistance by additional power optics. All they have to do is tip their head 15 degrees and they have the best optical assistance their body posses.

2. To remove and replace the comfort optics visor and achieve perfect vision every time. All the patient has to do is apply pressure to the expansion loop on the headband. When pressure is removed, the visor is in perfect alignment. When a surgeon needs additional optical assistance, he can align the visor with his arm and does not have to worry about contamination.

3. The elongated ports in the visor, with the aid of the alignment fixture, allows the patient to achieve perfect optical balance and does not have to accept what someone guesses is correct for the patient.

4. The comfort optics visor is the only optical device offered where the patient does all the selection, adjustment and alignment. Nobody can do it better than the patient.

5. The comfort optics visor is fitted with various power monoculars. They are extra close focus, to infinity, with roof-top prisms. If the patient has no primary vision, only peripheral vision, no matter how narrow the threshold of sight may be, the person can locate this threshold and prismatically take the preferrential vision, and superimpose this vision to primary vision. No other device can do this in a that achieved by the patient himself/herself.

6. The comfort optic visor is the only device that allows the patient to adjust the pupil to primary optic. This is very critical for some patients. Without this feature some patients would never be able to see.

DETAIL DESCRIPTION OF THE DRAWING

Figure 2:
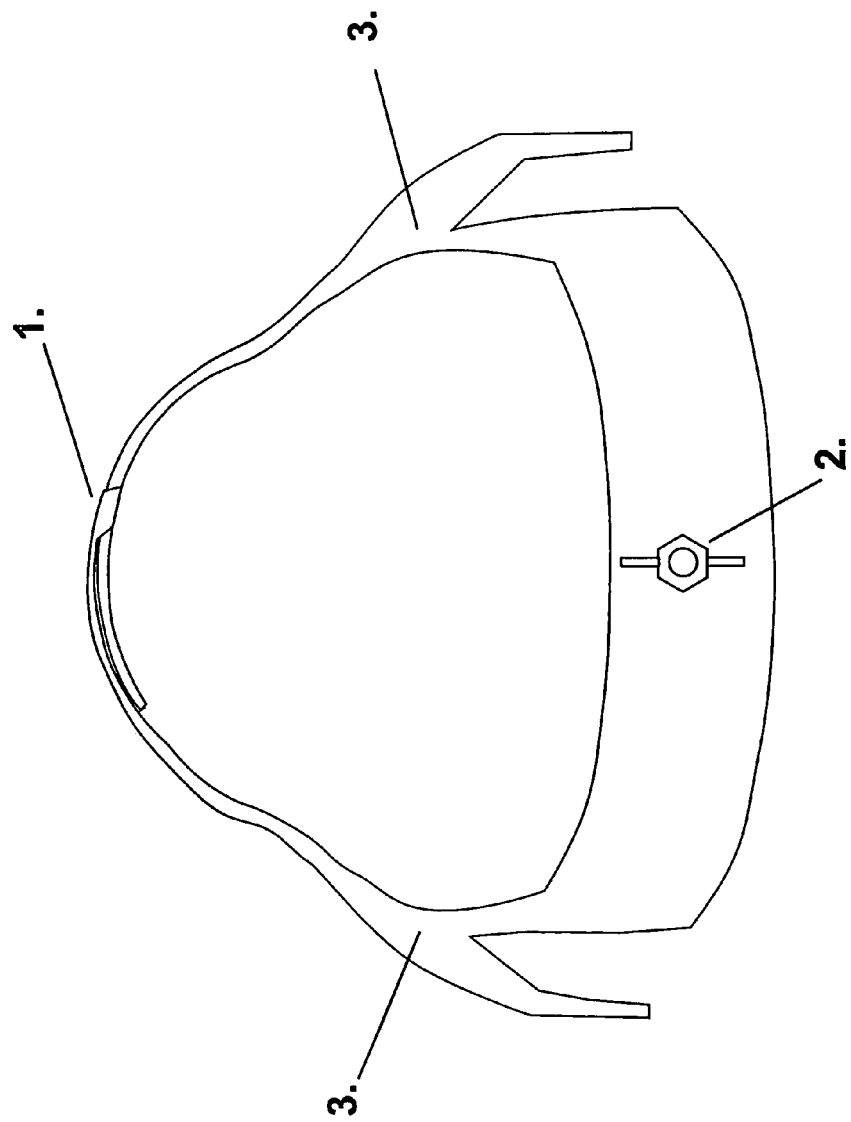
FIG. 2: The front view of the headband shows four attached bands that achieve perfect optical alignment. (Fasteners in front)
Figure 3:
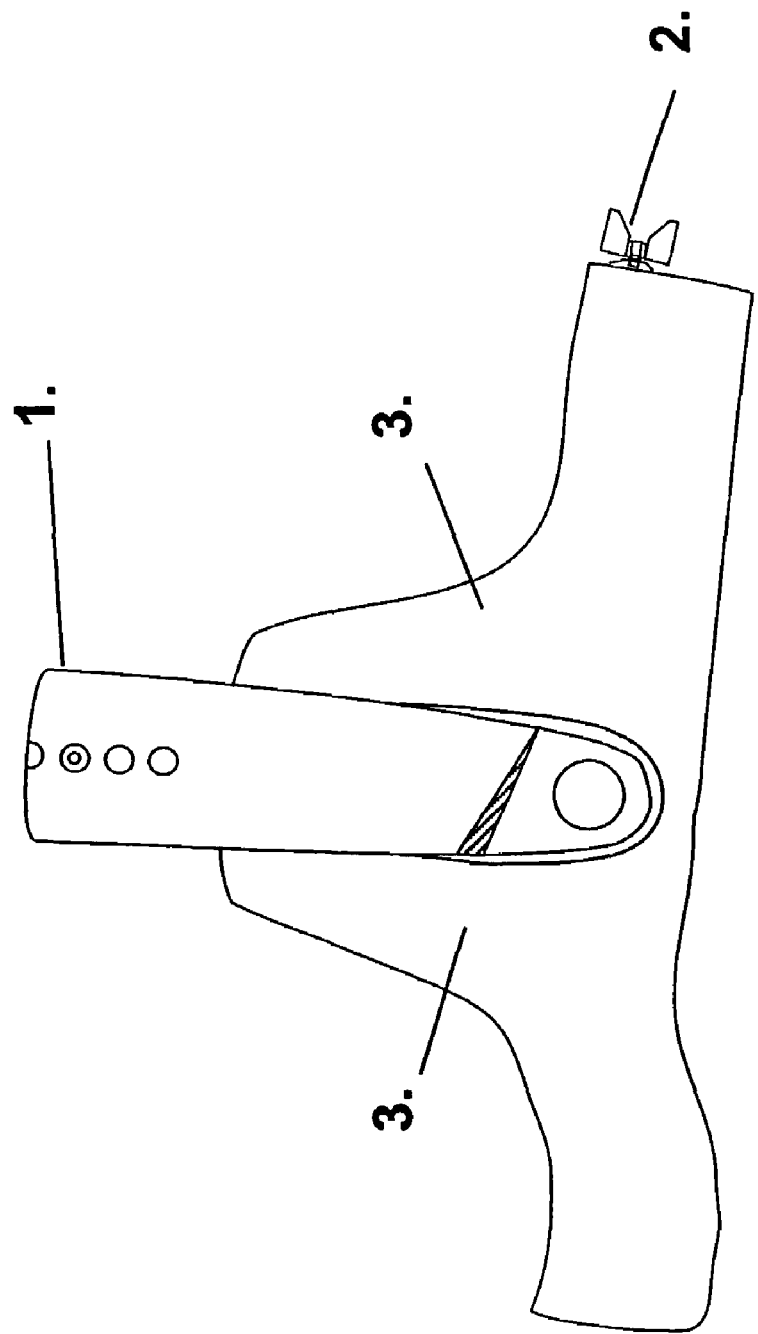
FIG. 3: The side view of the headband shows a fastener that allows adjustment and secures the visor to the headband, the attached bands, and the expansion loop.
Figure 4:
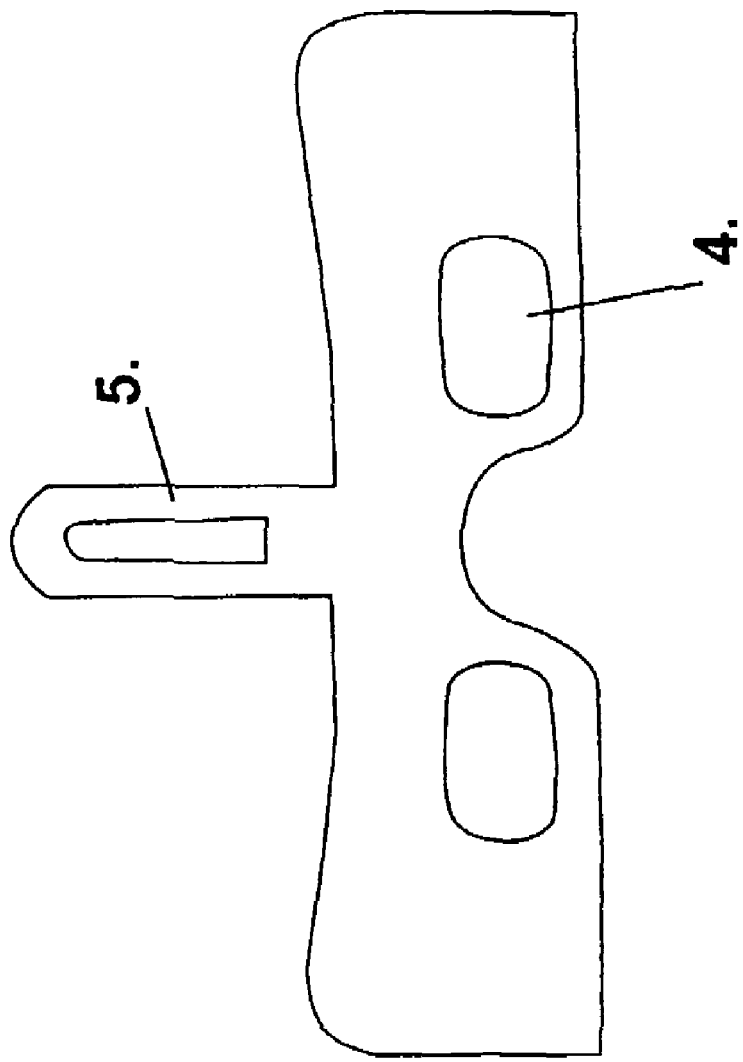
FIG. 4: The front view of the visor shows the visor's elongated mounting ports to accommodate either fixed, adjustable mechanical or electronic monoculars. The elongated parts allow for adjustment to the patient's center distance.
Figure 5:
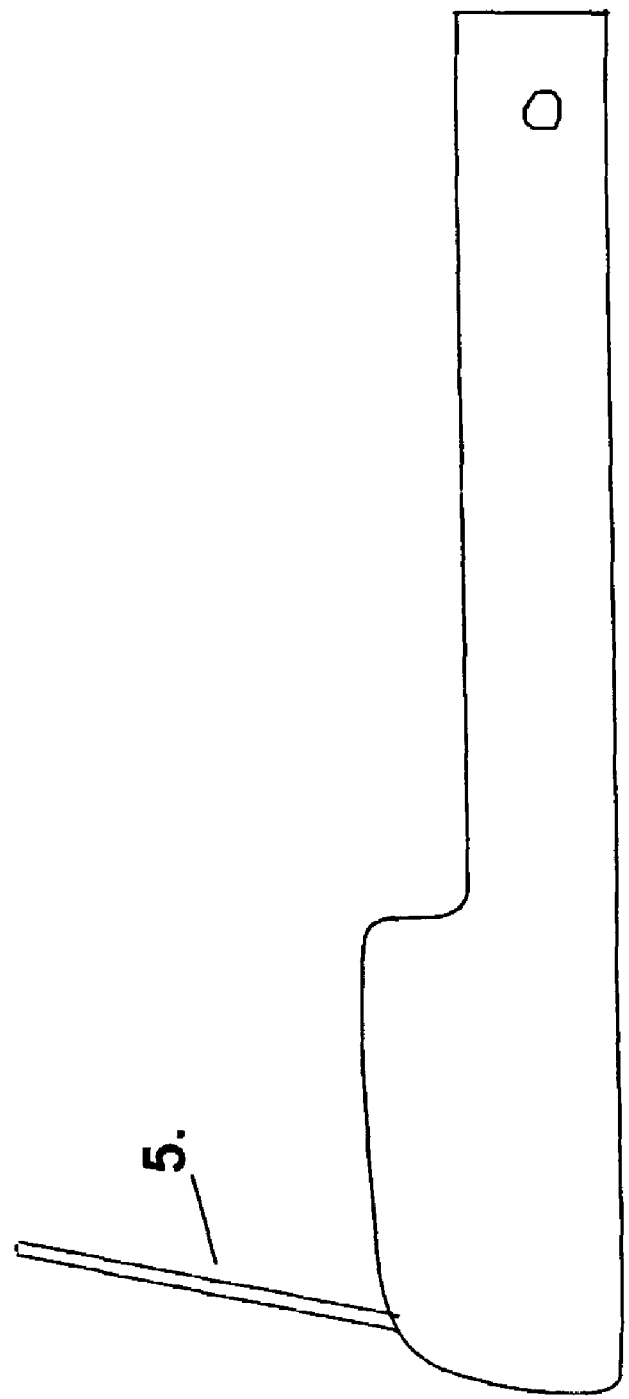
FIG. 5: The side view of the visor shows an elongated bracket in the front. The bracket is elongated to allow for proper adjustment alleviation of any cantilever effect from heavy monoculars. It maintains stability.
Figure 6:
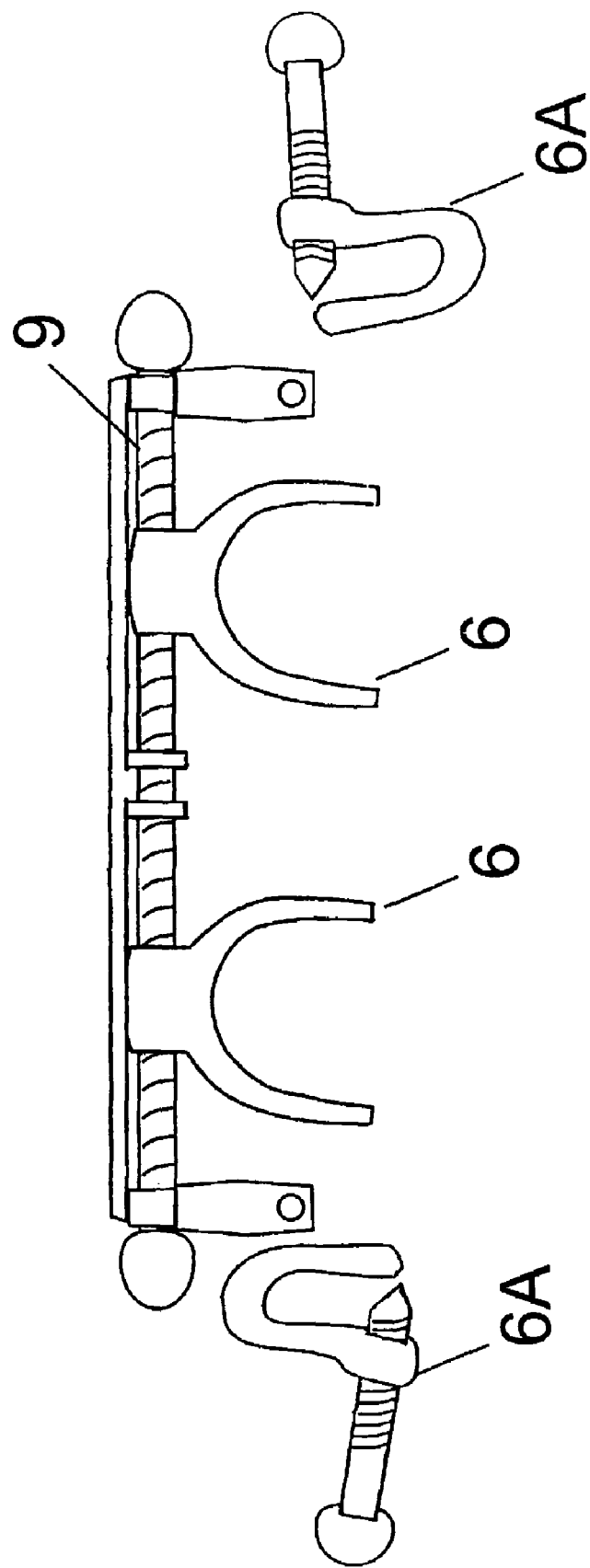
FIG. 6: The front view of the alignment adjuster shows a fixture that is temporarily attached to the visor, allowing the patient to independantly adjust each monocular to achieve the maximum vision the patient can obtain. It is used to rotate the monocular to achieve superimposure using rooftop prismatic monocular. When alignment is achieved, the fixture is removed.
Figure 7:
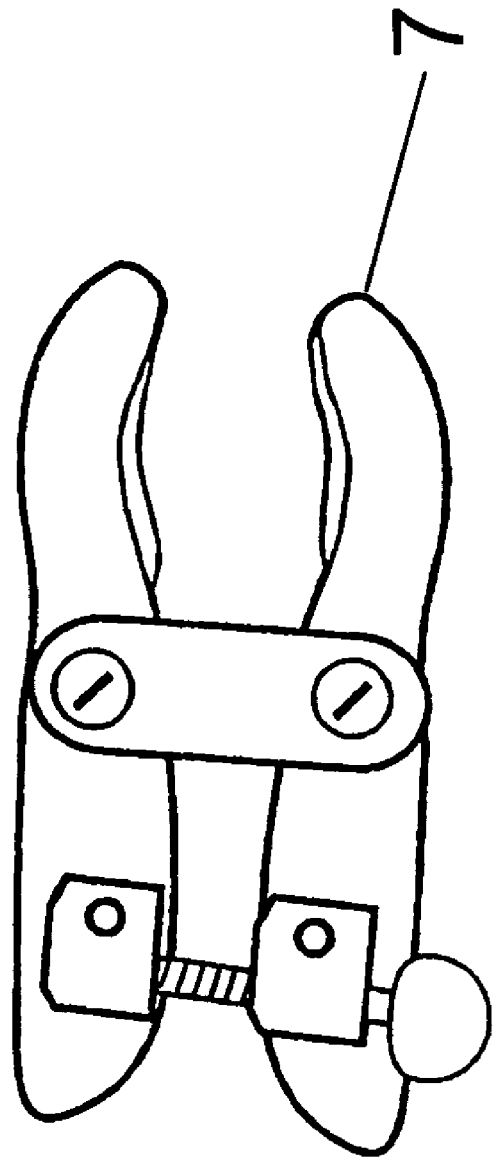
FIG. 7: The front view of the alignment clamp shows a clamp that is attached to the monocular, while being held in place by FIG. 6, to maintain alignment. If patient's center vision is lost, the peripheral vision can be superimposed over the primary vision.
Figure 8:
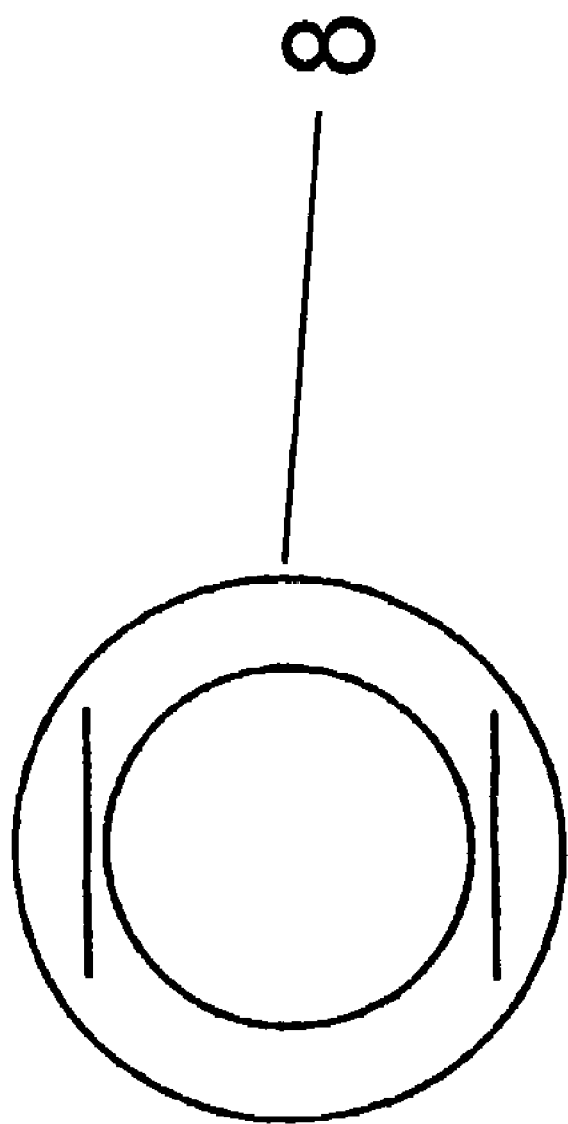
FIG. 8: The top view of the beveled adjuster shows a bevel that converts a view visor into a reading visor. The splines maintain the correct angularity for reading.
Figure 9:
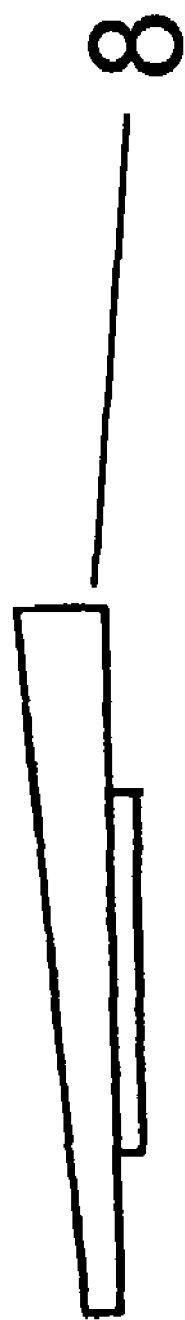
FIG. 9: The side view of the beveled adjuster.

FIGS. 1, 2, and 3 are the side views of the headband. In these figures (1) is the head, (2) the fastener, and (3) are the two tabs on the side of the visor. FIGS. 4 and 5 are the front and side views of the visor. These figures comprise the elongated adjusting ports (4) and the elongated bracket (5). FIGS. 6 and 7 are the front views of the alignment adjuster. These figures comprise an adjustment bar tool (9) and rotating clamps (6) and (6A) FIGS. 8 and 9 are the top and side views of the beveled adjuster, where (8) is a lens.

The comfort optics visor is worn with a vertical support band running over the top of the head (1). A supporting band around the head incorporates the elongated brackets (5) and the fastener (2), which fix the visor in place the visor moves at a fulcrum over each ear. Two tabs on each side (3) near the fulcrum lock the position of the visor so that the same fit can be achieved each time the visor is worn. The optics mount to the front of the visor in elongated adjusting ports (4) two tools are used to allign the visor and the optics (6&7). When the visor is coverted for reading two plastic wedges are placed at each monocular to converge the lenses (8).

The invention claimed is:

1. A headband comprising an expansion loop adapted to run from one side of the head over the top of the head to the other side of the head, the expansion loop being split at each side of head
   a back loop adapted to run around the back of the head
   a front loop adapted to run from one side of the head across the wearers forehead to the other side of the head
   integrally attached side bands extending outward from at each side of said expansion loop, each side band being attached to said expansion loop at its upper end at said split and terminating in a free distal end.

2. The headband of claim 1 further comprising a visor having a front piece adapted to be positioned in front of the wearer's eyes, and side pieces each of which extend from the front piece to the free distal end of said side band, and being rotatably attached to said band, said front piece carrying at its center an upwardly projecting slotted member, said front loop of said headband further having a fastening means which adjustably engages with said slot member so that the visor may be rotated up or down to suit the wearer and then said fastening means being set to fix the up and down position of said visor.

3. The headband of claim 2 still further comprising said center piece of said visor having two spaced apart elongated mounting ports adapted to be positioned before the wearers eyes and each having received therein one viewing end of a monocular, said front piece carrying an alignment adjustment support said alignment support comprising:
   (i) two outwardly extending projections above and at each side of each monocular,
   (ii) a threaded member carried at each of its ends above each monocular by said outwardly extending projections,
   (iii) threadably movable on and carried by each said threaded member a means for engaging the exterior surface of said monocular so that when said threaded member is rotated, said monocular is laterally moved within said elongated mounting port.

* * * * *